US 8,568,412 B2

Oct. 29, 2013

(12) United States Patent
Brandt et al.

(54) APPARATUS AND METHOD OF CONTROLLING CUTTING BLADE TRAVEL THROUGH THE USE OF ETCHED FEATURES

(75) Inventors: Kim V. Brandt, Laporte, CO (US); Allan G. Aquino, Longmont, CO (US)

(73) Assignee: Covidien LP, Mansfield, MA (US)

(*) Notice: Subject to any disclaimer, the term of this patent is extended or adjusted under 35 U.S.C. 154(b) by 909 days.

(21) Appl. No.: 12/556,407

(22) Filed: Sep. 9, 2009

(65) Prior Publication Data

US 2011/0060334 A1    Mar. 10, 2011

(51) Int. Cl.
*A61B 18/14* (2006.01)

(52) U.S. Cl.
USPC .................................. 606/51; 606/205

(58) Field of Classification Search
USPC .............. 606/50–52, 167, 205–209
See application file for complete search history.

(56) References Cited

U.S. PATENT DOCUMENTS

| | | | |
|---|---|---|---|
| 5,797,938 | A | 8/1998 | Paraschac et al. |
| 7,232,440 | B2 | 6/2007 | Dumbauld et al. |
| 7,442,194 | B2 | 10/2008 | Dumbauld et al. |
| 7,481,810 | B2 | 1/2009 | Dumbauld et al. |
| 7,487,780 | B2 | 2/2009 | Hooven |
| 7,887,536 | B2 | 2/2011 | Johnson et al. |
| 8,016,827 | B2 | 9/2011 | Chojin |
| 8,112,871 | B2 | 2/2012 | Brandt et al. |
| 8,114,122 | B2 | 2/2012 | Nau, Jr. |
| 8,133,254 | B2 | 3/2012 | Dumbauld et al. |
| 8,142,473 | B2 | 3/2012 | Cunningham |
| 8,162,965 | B2 | 4/2012 | Reschke et al. |
| 8,162,973 | B2 | 4/2012 | Cunningham |
| 8,197,479 | B2 | 6/2012 | Olson et al. |
| 8,226,650 | B2 | 7/2012 | Kerr |
| 8,251,994 | B2 | 8/2012 | McKenna et al. |
| 8,257,387 | B2 | 9/2012 | Cunningham |
| 8,266,783 | B2 | 9/2012 | Brandt et al. |
| 2003/0139742 | A1 | 7/2003 | Wampler et al. |
| 2005/0004569 | A1 | 1/2005 | Witt et al. |
| 2006/0189980 | A1* | 8/2006 | Johnson et al. .............. 606/51 |
| 2007/0043352 | A1 | 2/2007 | Garrison et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley
*Assistant Examiner* — Samantha Good

(57) ABSTRACT

A forceps includes a housing including a shaft. The shaft includes an end effector assembly having a pair of curved jaw members. The jaw members include an electrically conductive surface and a curved blade channel having opposing sidewalls. A cutting blade is configured for translation within the blade channel. Proximal portions of a first sidewall include incident angles of less than five degrees that engage the cutting blade and direct the blade towards a specific point of contact on the opposing sidewall of the curved blade channel.

19 Claims, 13 Drawing Sheets

(56) References Cited

U.S. PATENT DOCUMENTS

| | | |
|---|---|---|
| 2007/0173814 A1 | 7/2007 | Hixson |
| 2008/0319442 A1 | 12/2008 | Unger et al. |
| 2009/0012520 A1 | 1/2009 | Hixson et al. |
| 2009/0112206 A1 | 4/2009 | Dumbauld et al. |
| 2009/0182327 A1 | 7/2009 | Unger |
| 2010/0016857 A1 | 1/2010 | McKenna et al. |
| 2010/0023009 A1 | 1/2010 | Moses et al. |
| 2010/0036375 A1 | 2/2010 | Regadas |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0094287 A1 | 4/2010 | Cunningham et al. |
| 2010/0100122 A1 | 4/2010 | Hinton |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0249769 A1 | 9/2010 | Nau, Jr. et al. |
| 2010/0274244 A1 | 10/2010 | Heard |
| 2010/0280511 A1 | 11/2010 | Rachlin et al. |
| 2011/0015632 A1 | 1/2011 | Artale |
| 2011/0034918 A1 | 2/2011 | Reschke |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| EP | 1 649 821 A1 | 4/2006 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparooscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

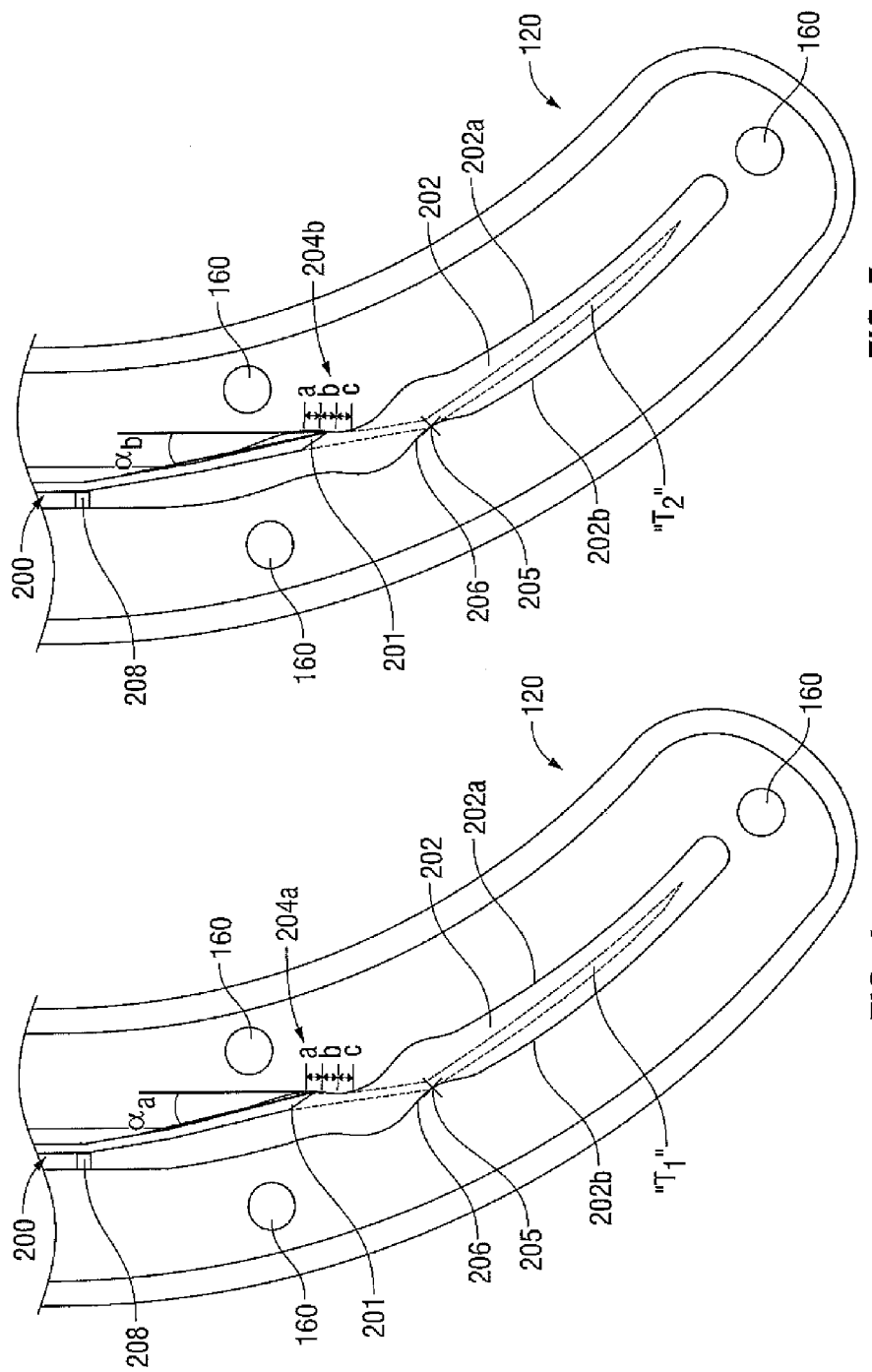

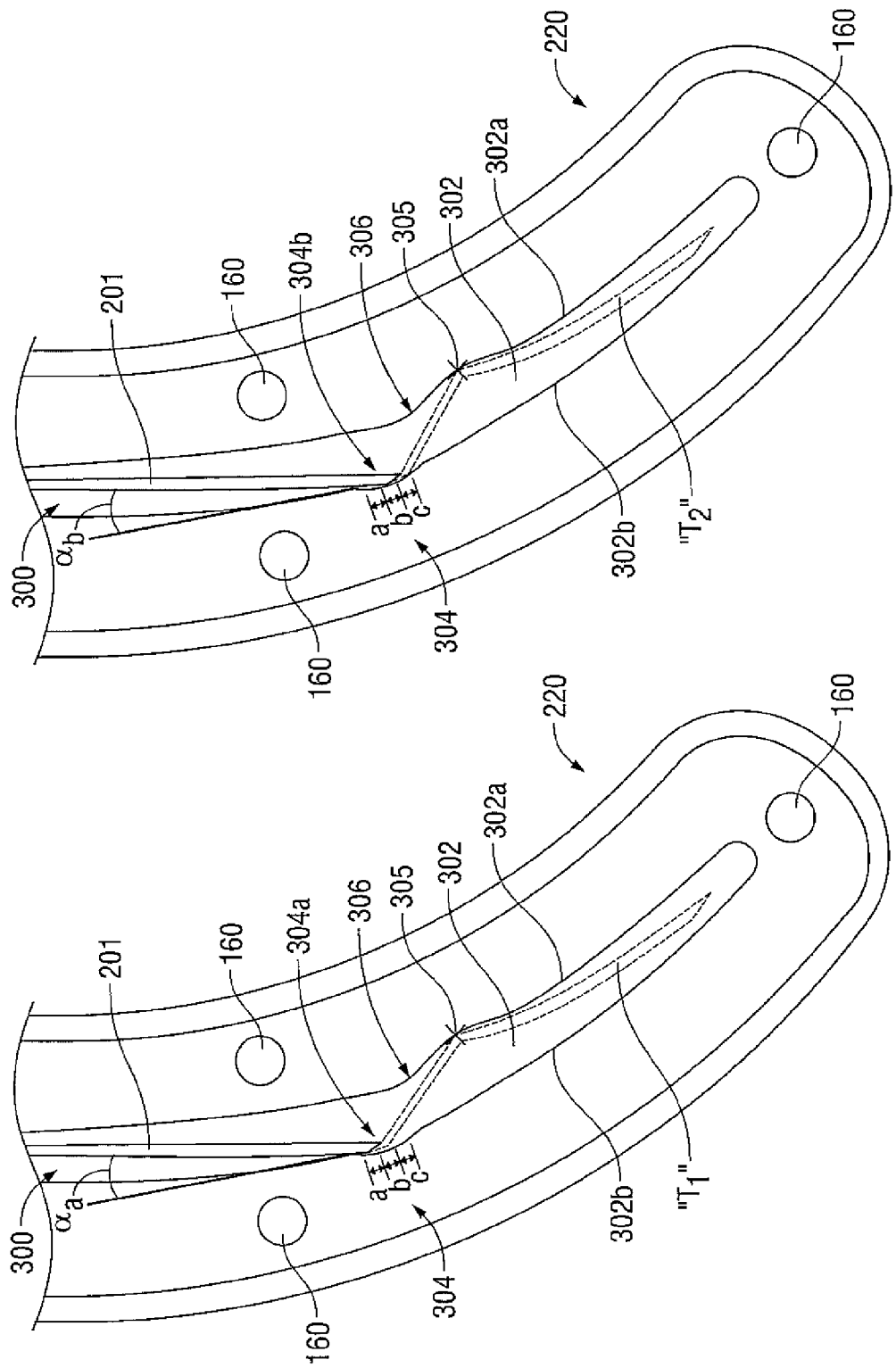

APPARATUS AND METHOD OF CONTROLLING CUTTING BLADE TRAVEL THROUGH THE USE OF ETCHED FEATURES

BACKGROUND

1. Technical Field

The present disclosure relates to an apparatus and method of controlling cutting blade travel in a surgical instrument. More particularly, the present disclosure relates to an apparatus and method of controlling cutting blade travel through the use of etched features using photolithography.

2. Background of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, fuse, seal, cut, desiccate, and/or fulgurate tissue.

As an alternative to open electrosurgical forceps for use with open surgical procedures, many modern surgeons use endoscopes and endoscopic electrosurgical apparatuses (e.g., endoscopic or laparoscopic forceps) for remotely accessing organs through smaller, puncture-like incisions. As a direct result thereof, patients tend to benefit from less scarring, less pain, and reduced healing time. Typically, the endoscopic forceps is inserted into the patient through one or more various types of cannulas or access ports (typically having an opening that ranges from about five millimeters to about fifteen millimeters) that has been made with a trocar; as can be appreciated, smaller cannulas are usually preferred.

An endoscopic forceps that is configured for use with small cannulas (e.g., cannulas less than five millimeters) may present design challenges for a manufacturer of endoscopic instruments.

SUMMARY

Accordingly, the present disclosure is directed to a forceps having a cutting blade and an end effector assembly. The end effector assembly has a pair of jaw members selectively positionable relative to one another about a pivot. The jaw members may be curved. At least one of the curved jaw members includes an electrically conductive tissue engaging surface adapted to connect to an electrosurgical energy source. At least one of the jaw members includes a curved blade channel having opposing sidewalls defined therein and extending therealong.

The cutting blade is configured for selective translation within the curved blade channel and is formed by at least one of machining, photolithography and stamping. Proximal portions of a first sidewall are manufactured to include incident angles of less than five degrees that engage the cutting blade during translation thereof to direct the cutting blade towards a specific point of contact on the opposing sidewall of the curved blade channel. The specific point of contact on the opposing sidewall includes an incident angle of less than five degrees to further the cutting blade along the curved blade channel. One of the sidewalls is concave and the opposite sidewall is convex. The cutting blade is configured to engage and translate along the sidewalls in a substantially tangential manner. The cutting blade contacts the first sidewall of the cutting blade channel at an incident angle of less than five degrees and contacts the opposing sidewall of the cutting blade channel at an incident angle of less than five degrees. In one embodiment, the curved blade channel is manufactured by photolithography and the curved blade channel includes at least one etched feature that controls movement of the cutting blade along the curved blade channel. The etched feature(s) is disposed on the first sidewall and directs the cutting blade toward the specific point of contact on the opposing sidewall of the curved blade channel. The opposing sidewall includes one or more etched features that facilitate translation of the cutting blade along the curved blade channel in a substantially tangential manner.

In one embodiment, a cutting blade guide is disposed at a proximal end of the end effector assembly and is configured to guide the cutting blade towards the proximal portions of the first sidewall.

According to one aspect, the present disclosure is directed to a method of cutting tissue grasped between the jaws of a curved end effector of a forceps having a cutting blade, the curved end effector including a curved blade channel having opposing sidewalls defined therein and extending therealong. The method comprises the steps of: moving the cutting blade through the curved end effector until the cutting blade contacts a first sidewall at an incident angle of less than five degrees, the first sidewall forcing the cutting blade to towards a specific point of contact on the opposing sidewall of the curved blade channel; moving the cutting blade past the first sidewall, through the curved blade channel until the cutting blade contacts the specific point of contact on the opposing sidewall of the curved blade channel, the specific point of contact on the opposing sidewall of the curved blade channel forcing the cutting blade towards a second direction substantially parallel to the second wall; and moving the cutting blade along the second wall.

In one aspect, the present disclosure is directed to a method of manufacturing a curved knife channel defined within an end effector of a forceps. The method includes providing a resist covered substrate; providing a photolithography mask having a pattern configured to provide a curved blade channel defined in an end effector of the forceps; exposing the pattern of the photolithography mask to the resist covered substrate for developing the pattern on the resist covered substrate; and removing the exposed resist pattern to expose the curved blade channel of the end effector having first and second sidewalls, wherein proximal portions of the first sidewall are manufactured to include incident angles of less than five degrees to direct a translating cutting blade of the end effector towards a specific point of contact on the second, opposing sidewall of the curved blade channel.

BRIEF DESCRIPTION OF THE DRAWINGS

Various embodiments of the present disclosure are described hereinbelow with references to the drawings, wherein:

FIG. 4 is an enlarged, top plan view of the bottom jaw member of the end effector assembly of FIG. 3 showing a first travel path of the cutting blade;

FIG. 5 is an enlarged, top plan view of the bottom jaw member of the end effector assembly of FIG. 3 showing a second travel path of the cutting blade;

FIG. 12 is an enlarged, top plan view of one embodiment of the bottom jaw member of the end effector assembly of FIG. 3 showing a first travel path of the cutting blade;

FIG. 13 is an enlarged, top plan view of the bottom jaw member of FIG. 12 showing a second travel path of the cutting blade.

DETAILED DESCRIPTION OF EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaws from an open to a closed configuration that forms a closed loop electrical circuit such that a desired tissue effect (e.g., tissue seal) may be achieved.

Figure 1:
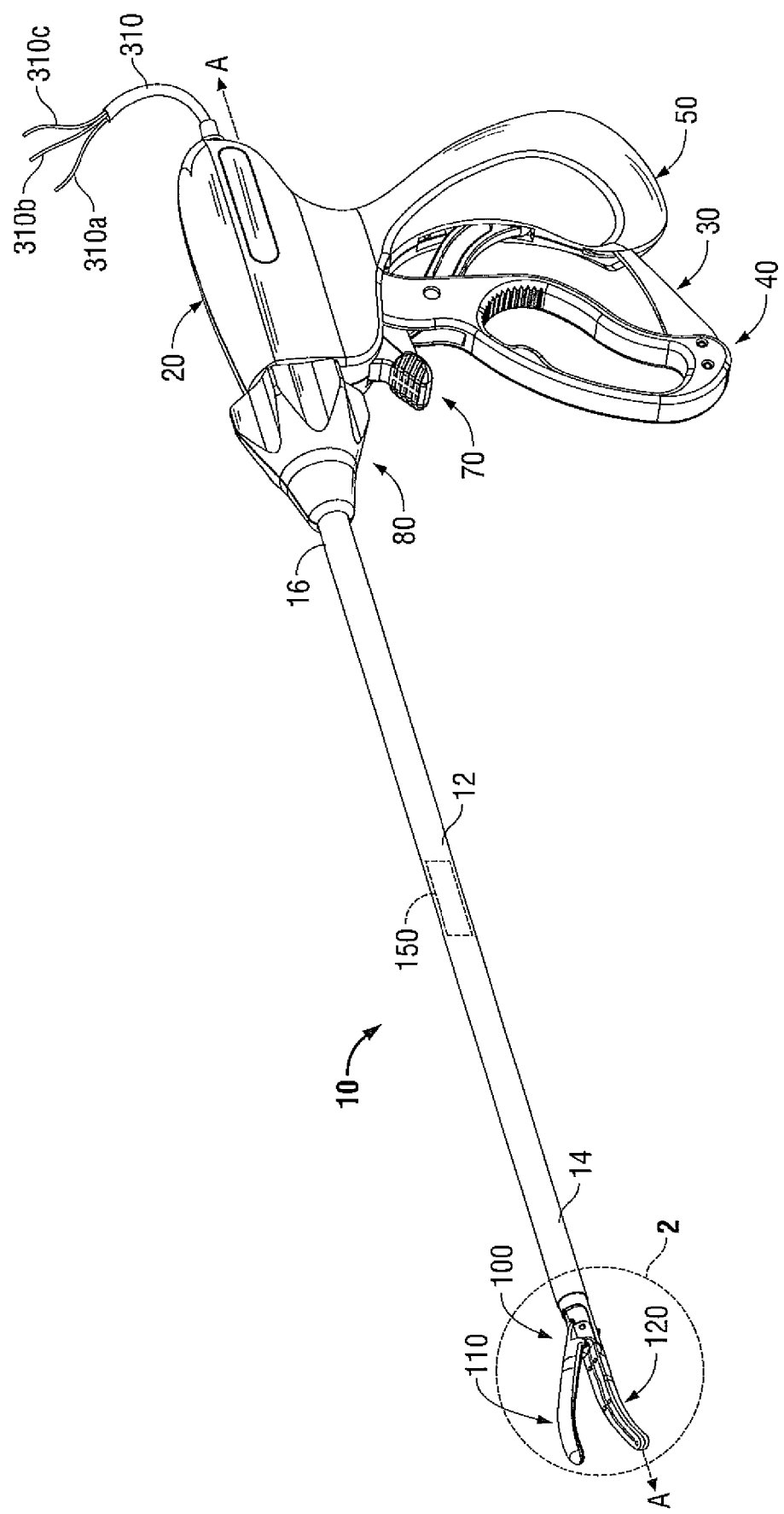
FIG. 1 is a right, perspective view of an endoscopic bipolar forceps showing a housing, a shaft, and an end effector assembly in accordance with the present disclosure.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of a laparoscopic instrument; however, it is contemplated that an open version of the forceps may also include the same or similar operating components and features as described below.

Forceps 10 includes a shaft 12 that has a distal end 14 configured to mechanically engage the end effector assembly 100 and a proximal end 16 that mechanically engages the housing 20. In the drawings and in the descriptions that follow, the term "proximal", as is traditional, will refer to the end of the forceps 10 that is closer to the user, while the term "distal" will refer to the end that is farther from the user.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033,399 entitled "ELECTROSURGICAL GENERATOR WITH ADAPTIVE POWER CONTROL". Cable 310 is internally divided into cable leads 310a, 310b, and 310c, which are designed to transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly-owned Patent Publication No., 2003-0229344, filed on Feb. 20, 2003, entitled "VESSEL SEALER AND DIVIDER AND METHOD OF MANUFACTURING THE SAME."

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A-A" (See FIG. 1).

As mentioned above, end effector assembly 100 is attached at the distal end 14 of shaft 12 and includes a pair of opposing curved jaw members 110 and 120. Movable handle 40 of handle assembly 30 is operatively connected to a drive assembly 150 (shown in phantom) that, together, mechanically cooperate to impart movement of the curved jaw members 110 and 120 from an open position wherein the curved jaw members 110 and 120 are disposed in spaced relation relative to one another, to a clamping or closed position wherein the curved jaw members 110 and 120 cooperate to grasp tissue therebetween. With this purpose in mind, drive assembly 150 may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

As shown best in FIGS. 2-3, 7, 9, 10A-10D, the end effector assembly 100 includes opposing curved jaw members 110 and 120 that cooperate to effectively grasp tissue for sealing purposes. The end effector assembly 100 may be designed as a unilateral assembly, e.g., curved jaw member 120 is fixed relative to the shaft 12 and curved jaw member 110 pivots about a pivot pin 103 relative to curved jaw member 120 to grasp tissue, or as a bilateral assembly, e.g., curved jaw members 110 and 120 pivot about pivot pin 103 relative to each other to grasp tissue. In some embodiments and as will be discussed in further detail below, curved jaw members 110, 120 are operably coupled to each other via pivot pin 103 which allows jaw member 110 to pivot relative to stationary curved jaw member 120. In some embodiments, fixed curved jaw member 120 may be monolithically formed with shaft 12, e.g., stationary curved jaw member 120 may be defined by the distal end 14 of shaft 12.

Pivoting curved jaw member 110 may be formed from any suitable material, for example without limitation, metallic material such as aluminum and alloys thereof, plated brass, stainless steel, stainless steel alloys, beryllium copper, etc. In other embodiments, one or both curved jaw members 110 and 120 may be formed from material having malleable or flexible properties or, alternatively, one or both of curved jaw members 110 and 120 may be formed from a material having inflexible properties. In yet another embodiment, the distal end of the jaw 110 is configured to engage and/or grasp tissue prior to a middle portion and/or a proximal or "rear" end of the jaw 110, which is termed "tip-biased." More specifically, after the distal end of curved jaw member 110 engages tissue, the middle and/or proximal end of curved jaw member 110 are then caused to rotates inward toward the fixed curved jaw member 120 such that tissue may be grasped therebetween. The curved jaw member 110 operates to allow precision generation of pressure on tissue grasped between curved jaw members 110 and 120 for purposes of sealing the tissue, as will be discussed in more detail below.

Referring now to FIGS. 2-3, 7 and 9, curved jaw member 110 includes a pivot flange 118 having a mechanical interface 105 disposed thereon. Mechanical interface 105 may be, without limitation, a link, a gear, a pin, a rod, any combination thereof, or any interface suitable to operably couple pivot flange 118 to drive assembly 150. Pivot flange 118 also includes a pin slot 119 that is configured to engage pivot pin 103 to allow curved jaw member 110 to rotate relative to curved jaw member 120. More particularly, curved jaw member 120 includes a pair of proximal, upwardly extending flanges 125a and 125b which define a cavity 121 dimensioned to receive flange 118 of movable curved jaw member 110 therein. Each of the flanges 125a and 125b includes an aperture 101a and 101b, respectively, defined therethrough which secures pivot pin 103 on opposite sides of pivot mount 119 disposed within curved jaw member 110. As explained in further detail below, proximal movement of the drive assembly 150 engages mechanical interface 105 to pivot curved jaw member 110 to a closed position.

Figure 10A:
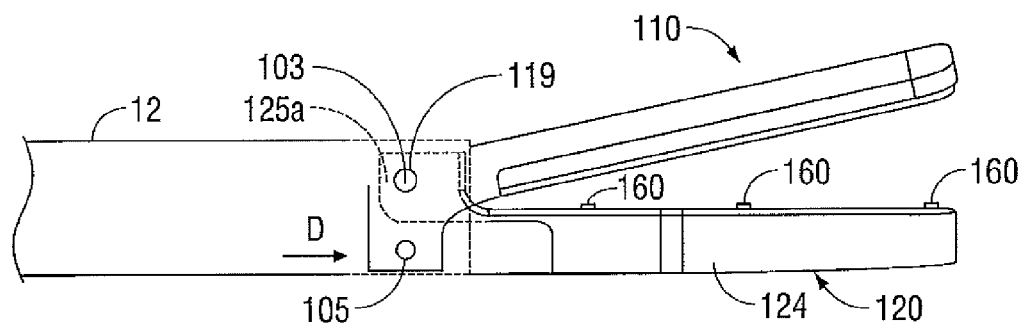
FIG. 10A is an enlarged, side view of the end effector assembly of FIGS. 1-3, 7 with the jaw members shown in the open configuration.
Figure 10B:
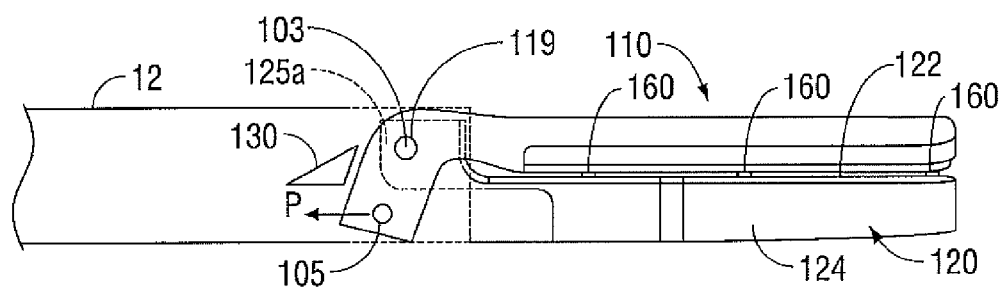
FIG. 10B is an enlarged, side view of the end effector assembly of FIGS. 1-3, 7 with the jaw members shown in a closed configuration.

As best shown in FIGS. 10A and 10B, mechanical interface 105 is operable by the drive assembly 150 such that drive assembly 150 urges mechanical interface 105 in the distal and proximal directions, as indicated by directional arrows "D" and "P", respectively. The pivoting curved jaw member 110 is actuated by the drive assembly 150 such that the pivoting curved jaw member 110 pivots about pivot pin 103 between open and closed positions. Pulling the mechanical interface 105 proximally closes the curved jaw members 110 and 120 about tissue grasped therebetween and pushing the mechanical interface 105 distally opens the curved jaw members 110 and 120 for grasping purposes. In another embodiment, illustrated in FIG. 10C, pivot pin 103 is configured to slide within a cam slot to pivot curved jaw member 110 between open and closed positions.

Figure 2:
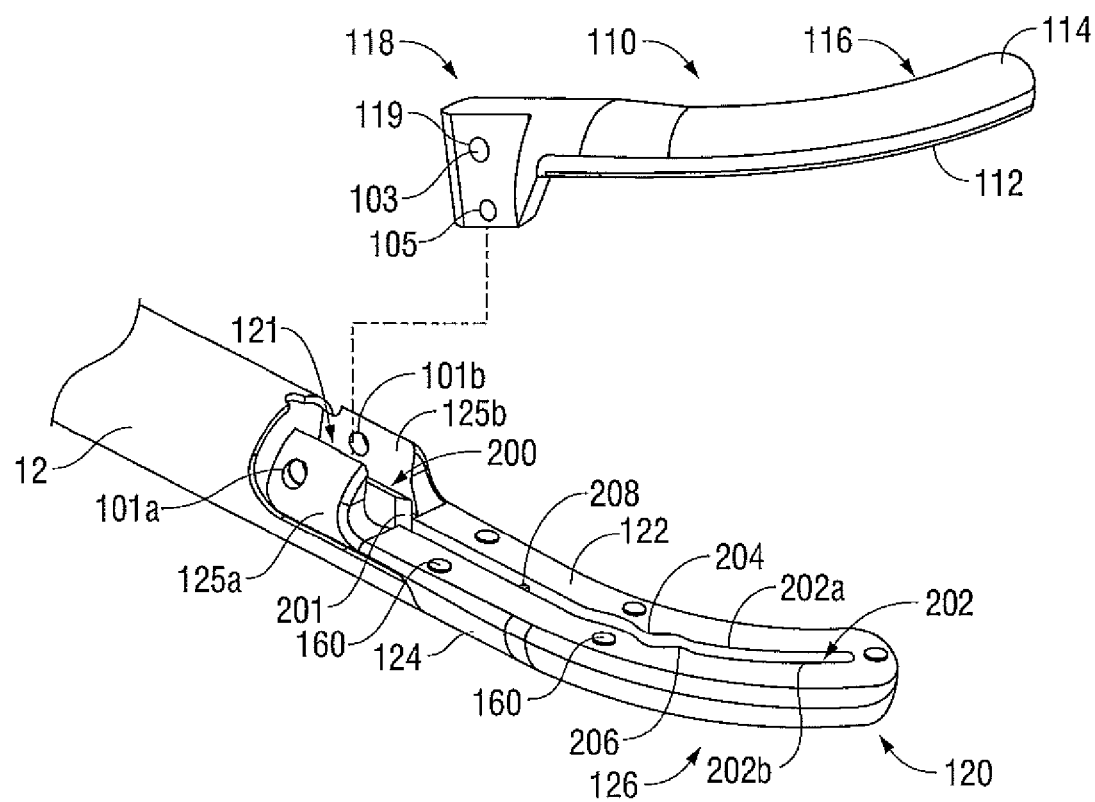
FIG. 2 is an enlarged, left perspective view of the end effector assembly of FIG. 1 with a top and a bottom jaw member shown in an open configuration and with a cutting blade of the jaw members shown in a first position.

As best shown in FIG. 2, curved jaw member 110 also includes a jaw housing 116 which has an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce curved jaw member 110 having an electrically conductive surface 112 which is substantially surrounded by an insulating substrate 114. The insulator 114, electrically conductive sealing surface 112 and the outer, non-conductive jaw housing 116 are configured to limit and/or reduce many of the known undesirable effects related to tissue sealing, e.g., flashover, thermal spread and stray current dissipation. In other embodiments, the curved jaw members 110 and 120 may be manufactured from a ceramic-like material and the electrically conductive surface(s) 112 are coated onto the ceramic-like curved jaw members 110 and 120.

Curved jaw member 120 includes similar elements to curved jaw member 110 such as jaw housing 126 having an insulator 124 and an electrically conductive sealing surface 122 that is dimensioned to securely engage the insulator 124.

Figure 3:
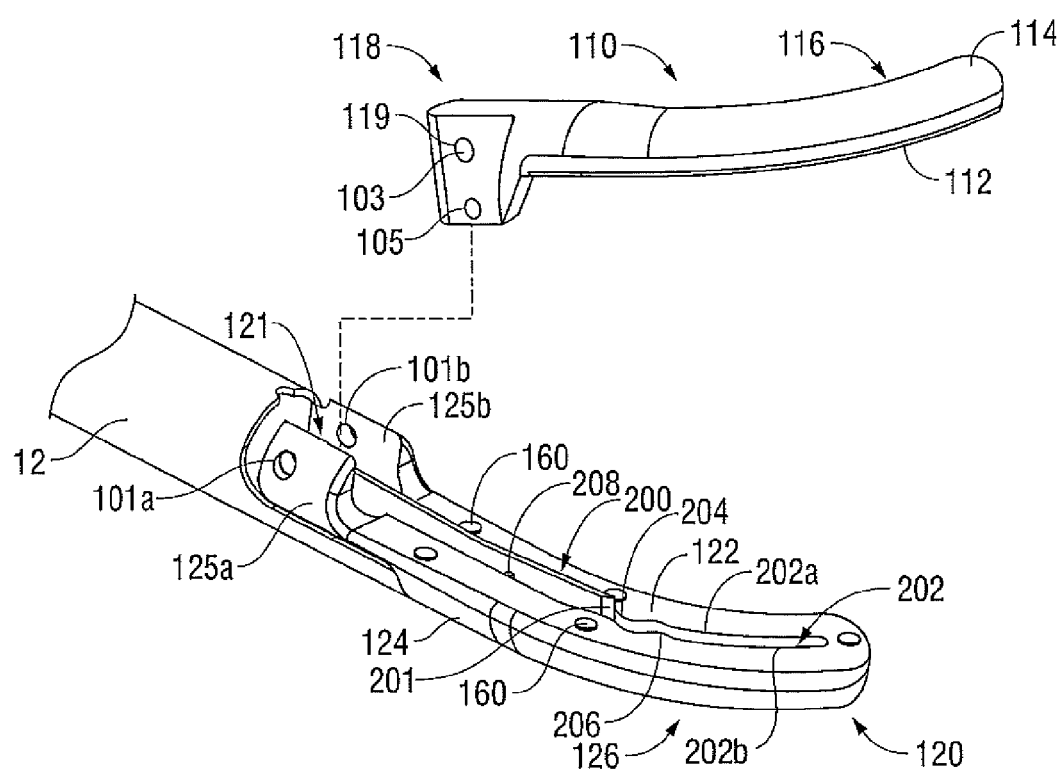
FIG. 3 is an enlarged, left perspective view of the end effector assembly of FIGS. 1-2 with the jaw members shown in the open configuration and with the cutting blade of the jaw members shown in a second position.

As best shown in FIG. 2, curved jaw member 120 may include a series of stop members 160 disposed on the inner facing surfaces of the electrically conductive sealing surface 122 to facilitate gripping and manipulation of tissue and to define a gap "G" (FIG. 11) between opposing curved jaw members 110 and 120 during sealing and cutting of tissue. In embodiments, the gap distance between opposing sealing surfaces 112 and 122 during sealing ranges from about 0.001 inches to about 0.006 inches and, in other embodiments, between about 0.002 and about 0.003 inches. As best shown in FIG. 3, pivoting curved jaw member 110 pivots about pivot pin 103 to the closed position such that conductive sealing surface 112 engages stop members 160. The flexible nature of curved jaw member 110 allows an operator to generate additional sealing pressure on tissue grasped between the curved jaw members 110 and 120. More specifically, once end effector assembly 100 is in the closed position and pivoting curved jaw member 110 is engaged with stop members 160 (FIG. 10B), movable handle 40 may be squeezed relative to stationary handle 50 to utilize the flexibility of curved jaw member 110 to vary and/or generate additional closure pressure between curved jaw member 110 and stop members 160 for purposes of sealing tissue. The series of stop members 160 may be employed on one or both curved jaw members 110 and 120 depending upon a particular purpose or to achieve a desired result. A detailed discussion of stop members 160 as well as various manufacturing and assembling processes for attaching and/or affixing the stop members 160 to the electrically conductive sealing surfaces 112, 122 are described in commonly owned, co-pending U.S. Patent Publication Application No. 2004-0122423 entitled "VESSEL SEALER AND DIVIDER WITH NON-CONDUCTIVE STOP MEMBERS" by Dycus et al.

Figure 10C:
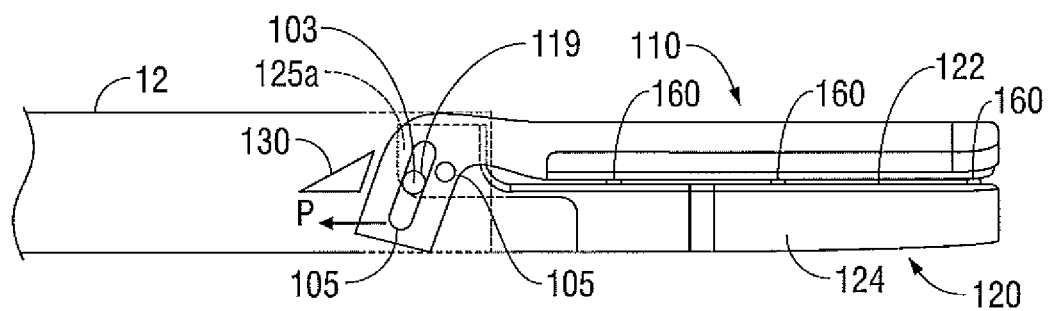
FIG. 10C is an enlarged, side view of an end effector assembly according to one embodiment of the present disclosure.

In some embodiments, as illustrated in FIGS. 10B and 10C, forceps 10 may include a camming member 130 disposed within shaft 12 and positioned to engage pivoting curved jaw member 110 at flange 118 when pivoting curved jaw member 110 is pivoted to the closed position. More specifically, as pivoting curved jaw member 110 pivots about pivot pin 103 from the open position to the closed position, e.g., in a clock-wise direction, camming member 130 cams a surface of flange 118 to prevent further pivoting of curved jaw member 110 about pivot pin 103 in the clock-wise direction. Once end effector assembly 100 is in the closed position, and camming member 130 is engaged with flange 118, movable handle 40 may be squeezed relative to stationary handle 50 to utilize the flexibility of curved jaw member 110 to vary and/or generate additional closure pressure between curved jaw members 110 and 120 and/or between curved jaw member 110 and stop members 160, as discussed hereinabove.

Figure 10D:
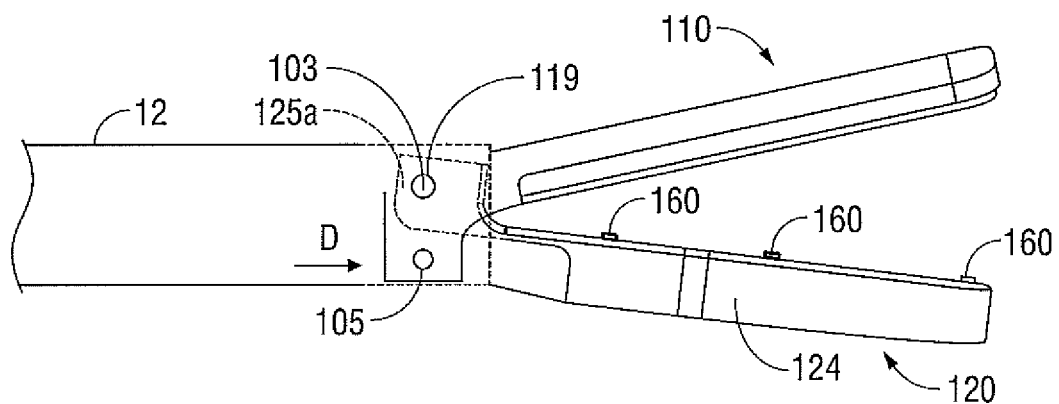
FIG. 10D is an enlarged, side view of an end effector assembly according to another embodiment of the present disclosure.

In some embodiments, as illustrated in FIG. 10D, the end effector assembly 100 may be designed as a bilateral assembly, e.g., each of curved jaw members 110 and 120 pivot about pivot pin 103 relative to each other to grasp tissue.

Figure 11:
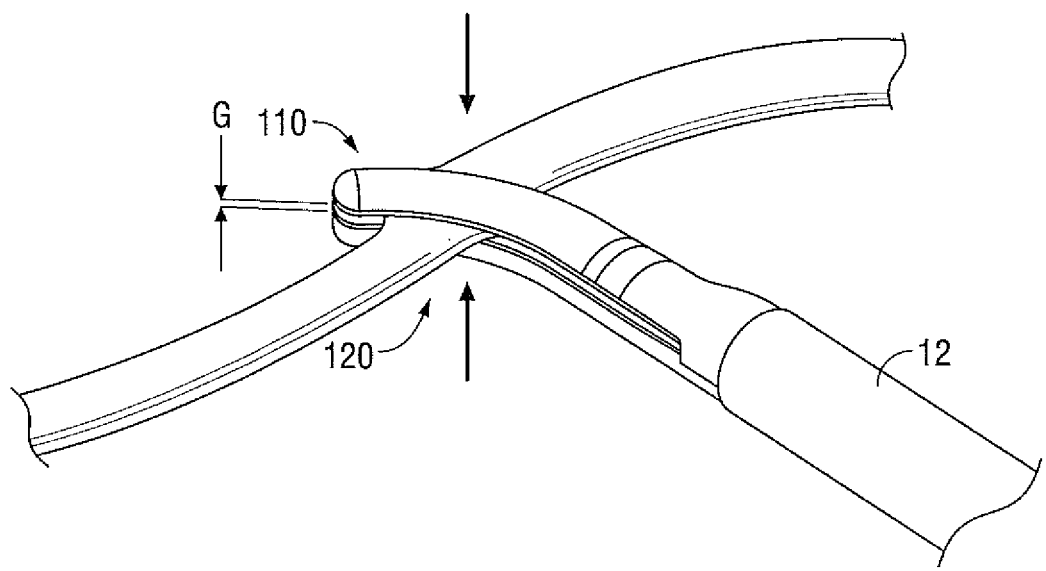
FIG. 11 is an enlarged, rear, perspective view of the end effectors shown grasping tissue.

FIG. 11 shows the forceps grasping tissue. As the handle 40 is squeezed, the mechanical interface 105 is pulled proximally by the movement of drive assembly 150 to rotate flange 118 clock-wise which, in turn, pivots curved jaw member 110 about pivot pin 103 to the closed position.

The mechanical advantage realized from the curved jaw member 110, as discussed hereinabove, will enable the operator to impart a load on the drive assembly 150 by squeezing handle 40 (e.g., through use of an operably coupled torsion spring). The drive assembly's 150 load is converted to a torque about the jaw pivot 103. As a result, a specific closure force can be transmitted to the opposing curved jaw members 110 and 120. Alternatively or additionally, stationary curved jaw member 120 may be formed from material having malleable or flexible properties to provide a mechanical advantage. Further, the curved jaw members 110 and 120 may be opened, closed and rotated via rotating assembly 80 to manipulate tissue until sealing is desired. This enables the user to position and re-position the forceps 10 prior to activation and sealing.

Once jaws members 110 and 120 are fully compressed about the tissue, the forceps 10 are now ready for selective application of electrosurgical energy and subsequent separation of the tissue.

The mechanical advantage provided by the one or both of curved jaw members 110 and 120 facilitates and assures consistent, uniform and accurate closure pressure about tissue within the desired working pressure range of about 3 kg/cm$^2$ to about 16 kg/cm$^2$ or preferrably, about 7 kg/cm$^2$ to about 13 kg/cm$^2$. By controlling the intensity, frequency and duration of the electrosurgical energy applied to tissue, the operator can cauterize, coagulate/desiccate, seal and/or simply reduce or slow bleeding.

As shown in FIGS. 2-9, a knife assembly 200 (operably associated with the trigger assembly 70), progressively and selectively divides tissue along a tissue plane in a precise manner to effectively divide the tissue. The knife assembly 200 includes a cutting blade 201 and a generally curved blade channel 202 extending along either one or both of the curved jaw members 110, 120. The cutting blade 201 is configured for selective translation within the curved blade channel 202. The curved blade channel 202 includes opposing first and second sidewalls 202a, 202b defined therein and extending therealong. The cutting blade 201 is configured to engage and translate along the opposing sidewalls 202a, 202b of the curved blade channel 202 in a generally tangential manner. The first sidewall 202a has a proximal etched concave feature 204 (or a plurality of etched concave features 204) and the second sidewall 202b has an etched convex feature 206 (or a plurality of etched convex features 206). Proximal etched concave features 204 of the first sidewall 202a are manufactured to include incident angles "a" of five degrees or less that engage the cutting blade 201 during translation thereof to direct the cutting blade 201 towards a specific point of contact 205 on the opposing second sidewall 202b of the curved blade channel 202 for facilitating the translation of the cutting blade 201 along the curved blade channel 202 in a generally tangential manner. The specific point of contact 205 disposed on the opposing second sidewall 202b includes an incident angle "a" of five degrees or less to further the cutting blade 201 along the curved blade channel 202 for facilitating the translation of the cutting blade 201 along the curved blade channel 202 in a generally tangential manner. For the purposes of clarity, the etched concave and convex features 204 and 206, respectively, are exaggerated for illustrative purposes.

A cutting blade guide 208 may be disposed at a proximal end of the end effector assembly 100. The cutting blade guide 208 is configured to guide the cutting blade 201 towards the proximal etched concave features 204 of the first sidewall 202a. Each etched feature 204, 206 is configured to control movement of the cutting blade 201 along the curved blade channel 202.

Figure 6:
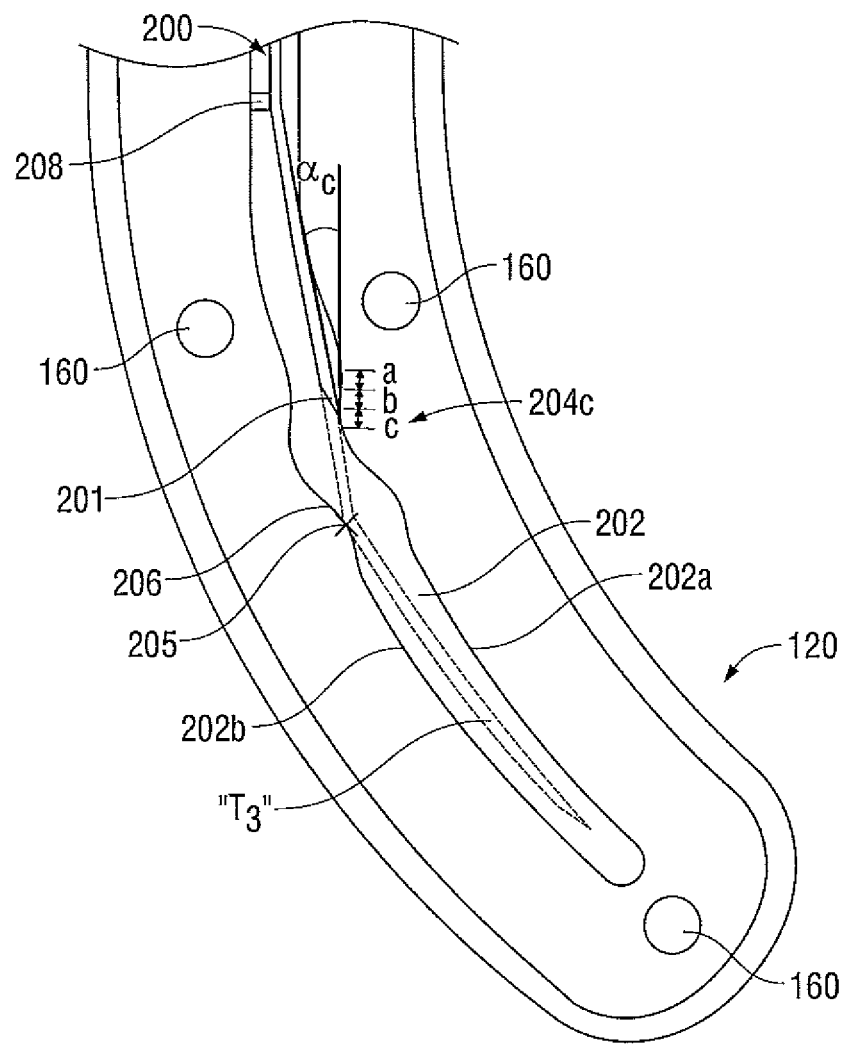
FIG. 6 is an enlarged, top plan view of the bottom jaw member of the end effector assembly of FIG. 3 showing a third travel path of the cutting blade.
Figure 7:
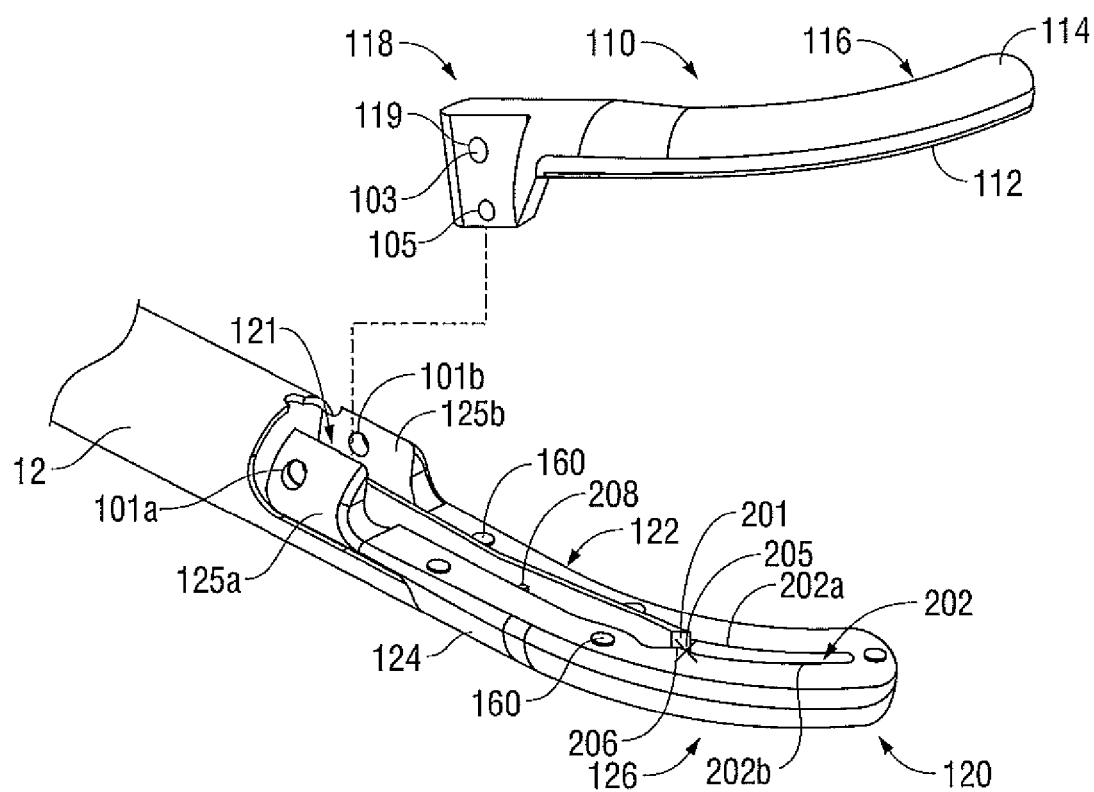
FIG. 7 is an enlarged, left perspective view of the end effector assembly of FIGS. 1-3 with the jaw members shown in the open configuration and with the cutting blade of the jaw members shown in a third position.

As shown in FIG. 2, the cutting blade 201 is disposed in a first position, which is an unactuated position. Upon actuation of the trigger assembly 70, the cutting blade 201 of the knife assembly 200 translates through the curved blade channel 202 (FIG. 3). Referring now to FIGS. 4-6, the cutting blade guide 208 guides the cutting blade 201 as it translates towards the proximal etched concave feature 204 of the first sidewall 202a of the cutting blade channel 202. Each of the cutting blade guide 208, the cutting blade 201, and the cutting blade channel 202 may be configured so that the cutting blade 201 may travel along a first (FIG. 4), second (FIG. 5), or third (FIG. 6) travel path "T1", "T2", "T3" toward the etched concave feature 204.

Figure 8:
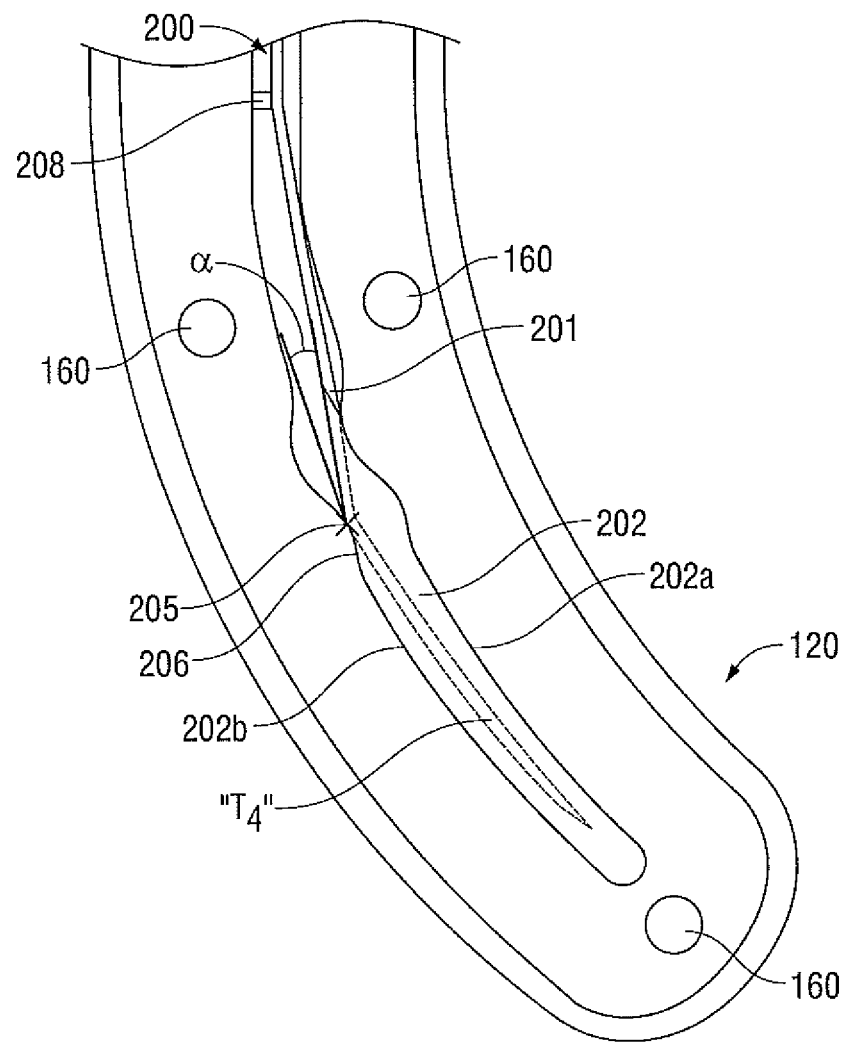
FIG. 8 is an enlarged, top plan view of the bottom jaw member of the end effector assembly of FIG. 7 showing a distal travel path of the cutting blade.
Figure 9:
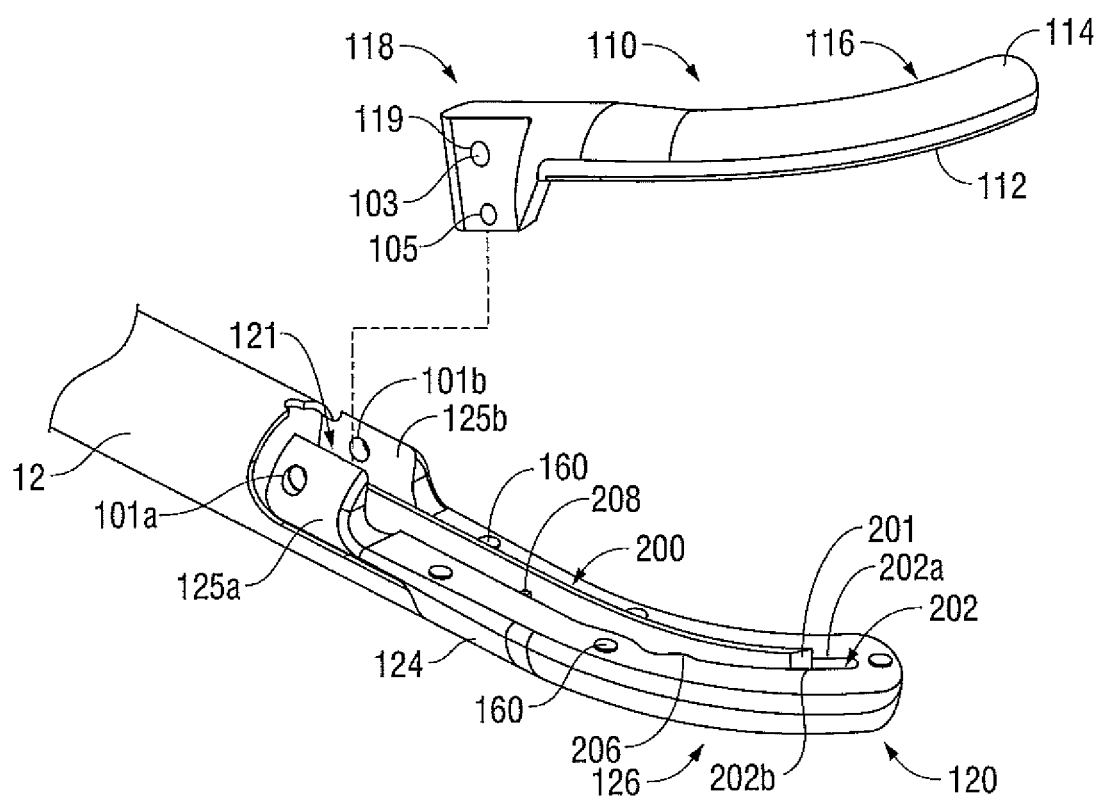
FIG. 9 is an enlarged, left perspective view of the end effector assembly of FIGS. 1-3, 7 with the jaw members shown in the open configuration and with the cutting blade of the jaw members shown in a fourth position.

From FIG. 4, the first travel path "T1" shows the cutting blade 201 engaging proximal concave feature 204 along a first portion 204a thereof having a length "a" at the incident angle "$\alpha_a$." Similarly, From FIG. 5, the second travel path "T2" shows the cutting blade 201 engaging concave feature 204 along a second portion 204b thereof having a length "b" at the incident angle "$\alpha_b$." From FIG. 6, the third travel path "T3" shows the cutting blade 201 engaging concave feature 204 along a third portion 204a thereof having a distance "c" at the incident angle "$\alpha_c$." The proximal etched concave feature 204 of the first sidewall 202a then directs the cutting blade 201 towards the specific point of contact 205 on the opposing second sidewall 202b of the curved blade channel 202 irrespective of where the cutting blade 201 contacts the concave feature 204a, 204b or 204c. In other words, the incident angle $\alpha_a$, $\alpha_b$, $\alpha_c$ of each portion 204a, 204b, 204c drives the blade 201 to the same point of contact 205 on the convex portion 206 to facilitate translation of the blade 201. Put simply, the specific point of contact 205 is the same location on the etched convex portion 206 of the opposing second sidewall 202b for each travel path "T1", "T2", "T3." Accordingly, the cutting blade 201 is then directed along the etched convex portion 206 towards the distal end of the opposing jaw members 110, 120 along the distal travel path "T4" as illustrated in FIGS. 8 and 9.

Figure 14:
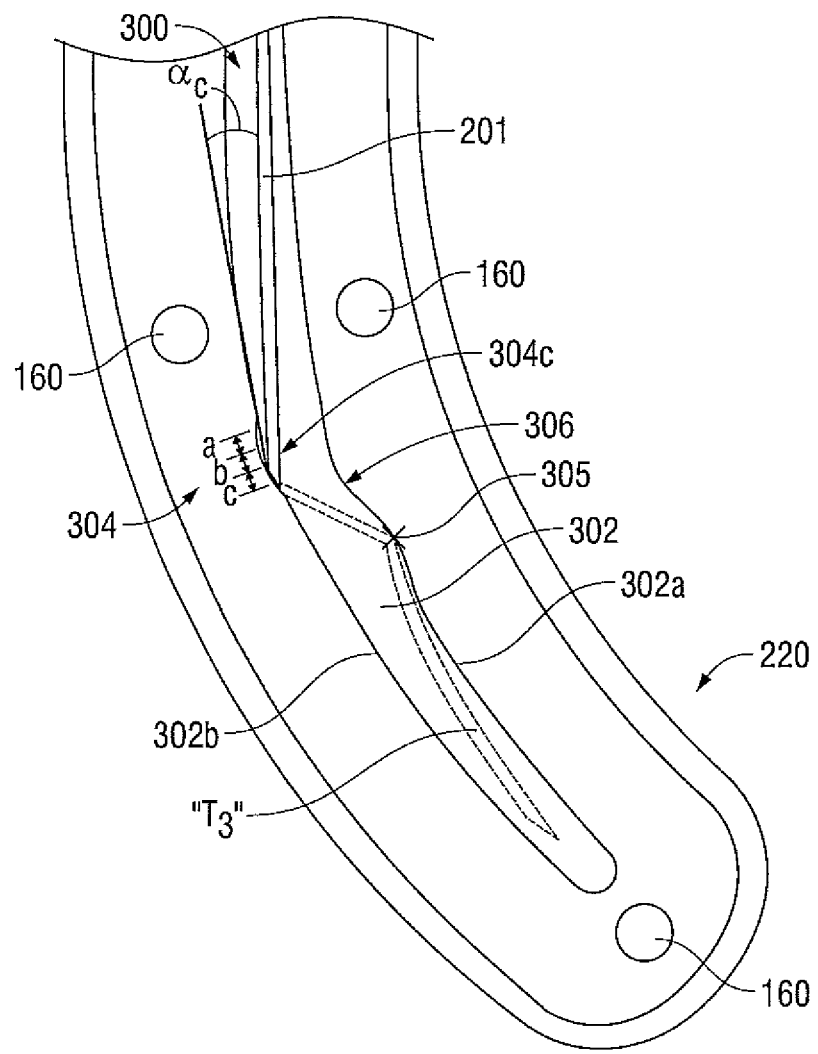
FIG. 14 is an enlarged, top plan view of the bottom jaw member of FIGS. 12 and 13 showing a third travel path of the cutting blade.

Referring now to FIGS. 12-14, one embodiment of a knife assembly 300 includes a cutting blade 201 and a generally curved blade channel 302 extending along either one or both of the jaw members 110, 120. The blade channel 302 includes opposing sidewalls 302a, 302b defined therein and extending therealong. The cutting blade 201 is configured to engage and translate along the opposing sidewalls 302a, 302b in a generally tangential manner. The side wall 302b has a proximal etched concave feature 304 (FIG. 12), or possibly, a plurality of proximal etched concave features, and the sidewall 302a has an etched convex feature 306, or possibly, a plurality of etched convex features. Each etched feature 304, 306 is manufactured to include incident angles of five degrees or less (e.g. "$\alpha_a$", "$\alpha_b$", and "$\alpha_c$") that engage the cutting blade 201 during translation thereof to direct the cutting blade 201 towards a specific point of contact 305 on the curved blade channel 302 for facilitating the translation of the cutting blade 201 along the curved blade channel 302 in a generally tangential manner. For the purposes of clarity, the etched concave and convex features 304 and 306, respectively, are exaggerated for illustrative purposes.

The cutting blade channel may be formed by one or more of the following manufacturing methods: machining, stamping, and photolithography. It is believed that the tolerances obtained by photolithography offer significant advantages over stamping or machining. In general, the steps of photolithography include providing a resist covered substrate; providing a photolithography mask having a predetermined pattern; exposing the pattern of the photolithography mask to the resist covered substrate for developing the pattern on the resist covered substrate; and removing the exposed resist pattern.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    an end effector assembly having a pair of jaw members selectively positionable relative to one another about a pivot, at least one of the jaw members including an electrically conductive tissue engaging surface adapted to connect to an electrosurgical energy source and at least one of the jaw members including a first sidewall and a second sidewall that together define a curved blade channel that extends between, and along, the first sidewall and the second sidewall, the first sidewall and the second sidewall being disposed opposite each other; and
    a cutting blade configured for selective translation within the curved blade channel;
    wherein a proximal portion of the first sidewall is manufactured to include an incident angle of less than five degrees that the cutting blade engages during translation thereof to direct the cutting blade towards a specific point of contact on the second sidewall of the curved blade channel;
    wherein the pair of jaw members are curved in a first direction away from a longitudinal axis defined by a shaft of the forceps at a first longitudinal location along the longitudinal axis, and wherein at the first longitudinal location along the longitudinal axis, the curved blade channel is curved in a second direction, the first direction and second direction being opposite directions.

2. The forceps according to claim 1, wherein the specific point of contact on the second sidewall includes another incident angle of less than five degrees to further advance the cutting blade along the curved blade channel.

3. The forceps according to claim 2, wherein one of the first sidewall and the second sidewall includes at least one concave portion and the other of the first sidewall and the second sidewall includes at least one convex portion.

4. The forceps according to claim 3, wherein one of the first sidewall and the second sidewall further includes at least one concave portion and at least one convex portion.

5. The forceps according to claim 4, wherein the first sidewall further includes at least one concave portion and at least one convex portion and the second sidewall further includes at least one concave portion and at least one convex portion.

6. The forceps according to claim 1, wherein the cutting blade channel is formed by at least one of machining, photolithography and stamping.

7. The forceps according to claim 1, wherein the cutting blade is configured to engage and translate along the sidewalls in a substantially tangential manner.

8. The forceps according to claim 1, wherein the jaw members are curved.

9. The forceps according to claim 1, wherein the curved blade channel is manufactured by photolithography and wherein the proximal portion of the first sidewall further includes at least one etched feature that is adapted to control movement of the cutting blade along the curved blade channel.

10. The forceps according to claim 9, wherein the at least one etched feature is adapted to direct the cutting blade toward the specific point of contact on the second sidewall as the cutting blade translates distally.

11. The forceps according to claim 9, wherein the second sidewall further includes at least one etched feature that facilitates substantially tangential translation of the cutting blade along the second sidewall.

12. The forceps according to claim 9, wherein the at least one etched feature is concave.

13. The forceps according to claim 9, wherein the at least one etched feature is convex.

14. The forceps according to claim 1, wherein the cutting blade contacts the first sidewall at the incident angle of less than five degrees and contacts the second sidewall at another incident angle of less than five degrees.

15. The forceps according to claim 1, further comprising a cutting blade guide disposed at a proximal end of the end effector assembly configured to guide the cutting blade towards the proximal portion of the first sidewall.

16. The forceps according to claim 1, wherein the first sidewall and the second sidewall further include a plurality of etched features that control movement of the cutting blade along the curved blade channel, each of the plurality of etched features being at least one of concave and convex.

17. The forceps according to claim 1, wherein at least one of the first sidewall and the second sidewall further includes plurality of peaks and valleys disposed at locations along the curved blade channel.

18. The forceps according to claim 1, wherein the curved blade channel is curved in the first direction at a second longitudinal location along the longitudinal axis, the at least one of the jaw member being curved in the first direction at the second longitudinal location along the longitudinal axis.

19. The forceps according to claim 18, wherein a curvature of the pair of jaw members is defined by a first radius extending from a first center point and wherein a curvature of the curved blade channel is defined by a second radius extending from a second center point, the first and second center points being offset at the first and second longitudinal locations.

* * * * *